(12) United States Patent
   Kaddoum

(10) Patent No.: US 12,599,737 B1
(45) Date of Patent: Apr. 14, 2026

(54) LARYNGOSCOPE BLADE WITH A CHANNEL

(71) Applicant: Roland Kaddoum, Riad el-Solh (LB)

(72) Inventor: Roland Kaddoum, Riad el-Solh (LB)

( * ) Notice: Subject to any disclaimer, the term of this patent is extended or adjusted under 35 U.S.C. 154(b) by 0 days.

(21) Appl. No.: 18/915,514

(22) Filed: Oct. 15, 2024

(51) Int. Cl.
   *A61M 16/04* (2006.01)

(52) U.S. Cl.
   CPC ... *A61M 16/0488* (2013.01); *A61M 2205/583* (2013.01); *A61M 2209/088* (2013.01); *A61M 2210/065* (2013.01)

(58) Field of Classification Search
   CPC ........ A61M 16/0488; A61M 2205/583; A61M 2209/088; A61M 2210/065; A61M 16/0497; A61M 16/0434; A61M 16/049; A61M 16/0409; A61M 2205/582; A61M 16/0816; A61M 16/0438; A61M 16/0459; A61M 16/0486; A61M 16/0415; A61M 16/0418; A61M 16/04; A61M 16/0402; A61M 16/0404; A61M 16/0445; A61M 16/0454; A61M 16/0484; A61M 16/0411; A61M 16/0427; A61M 16/0429; A61M 16/0465; A61H 7/00; A61J 15/00
   USPC ........................................ 128/200.23, 200.26
   See application file for complete search history.

(56) References Cited

U.S. PATENT DOCUMENTS

| | | | | |
|---|---|---|---|---|
| 3,856,001 A | * | 12/1974 | Phillips | A61B 1/267 600/199 |
| 6,142,144 A | | 11/2000 | Pacey | |
| 6,569,089 B1 | | 5/2003 | Covington et al. | |
| 8,529,442 B2 | | 9/2013 | Pacey et al. | |
| 8,663,099 B2 | | 3/2014 | Tydlaska et al. | |
| 8,998,804 B2 | | 4/2015 | Boedeker | |
| 10,213,567 B1 | * | 2/2019 | Theventhiran | .... A61M 16/0488 |
| 10,653,307 B2 | | 5/2020 | Molnar | |
| 11,497,394 B2 | | 11/2022 | Molnar | |
| 11,628,036 B2 | | 4/2023 | Molnar | |
| 2003/0078476 A1 | * | 4/2003 | Hill | A61B 1/267 600/109 |
| 2011/0077466 A1 | * | 3/2011 | Rosenthal | A61B 1/00096 600/188 |

(Continued)

FOREIGN PATENT DOCUMENTS

| | | |
|---|---|---|
| CN | 202180104822 2 A | 7/2024 |
| WO | WO2023/102891 A1 | 6/2023 |

*Primary Examiner* — Elliot S Ruddie

(74) *Attorney, Agent, or Firm* — Law Office of Vincent LoTempio, PLLC; Vincent G. LoTempio; Robert L. Cerasa

(57) ABSTRACT

The present disclosure relates to a laryngoscope blade modification for endotracheal intubation. The disclosure provides a flexible channel attached to the laryngoscope blade or a rigid channel that opens via a spring system. The channel further incudes a slit along the entire portion of the channel, enabling a guidewire to be loaded into the channel and advanced to a patient's vocal cords and trachea before being dislodged or removed in a quick, efficient manner. An endotracheal tube is then slided over the guidewire into the vocal cords and trachea. Once endotracheal tube is inserted, guidewire is removed and intubation initiated. The present disclosure enables a faster insertion of a guidewire into the vocal cords over conventional methods without wasting precious seconds. By using a guidewire with a soft tip, the incidence of vocal cord injury decreases substantially and intubation performed successfully in a quick manner.

13 Claims, 10 Drawing Sheets

(56)            References Cited

U.S. PATENT DOCUMENTS

| | | | | |
|---|---|---|---|---|
| 2014/0345622 | A1* | 11/2014 | Vilasi | A61M 16/0816 |
| | | | | 128/207.14 |
| 2019/0125177 | A1* | 5/2019 | Sutherland | A61B 1/0014 |
| 2020/0113427 | A1* | 4/2020 | Molnar | A61M 16/0463 |
| 2021/0361895 | A1* | 11/2021 | Nekhendzy | A61B 1/00009 |
| 2022/0110514 | A1* | 4/2022 | Molnar | A61B 1/00073 |
| 2023/0166066 | A1* | 6/2023 | Taicher | A61M 16/0488 |
| | | | | 128/200.26 |
| 2023/0404384 | A1 | 12/2023 | Siebenhaar | |

* cited by examiner

104

102

101

LARYNGOSCOPE BLADE WITH A CHANNEL

BACKGROUND OF THE INVENTION

Field of the Disclosure

The present disclosure relates to laryngoscope blade modification for endotracheal intubation. In particular, the present disclosure relates to laryngoscope blade with flexible channel with a slit to facilitate the endotracheal intubation. The channel also can be rigid, made from the same material of the blade and opens via a spring system.

General Background

Endotracheal intubation, or intubation, is a medical procedure that involves inserting a flexible plastic tube into a patient's windpipe (trachea). The number of intubations performed annually in the United States is between 13 and 20 million. According to an updated report by the American Society of Anesthesiologists Task Force on Difficult Airway Management in 2002, difficult laryngoscopy is defined as not being able to visualize any portion of the vocal cords after multiple attempts at conventional laryngoscopy, whereas difficult intubation is defined as tracheal intubation that requires multiple attempts, in the presence or absence of tracheal pathology. Adnet et. al. found that the incidence of difficult laryngoscopy ranges between 10.7% in the simple extension position and 11.4% in the sniffing position. The overall incidence of difficult intubation was found to be 5.8% in subjects who have no pathologic airway anatomy, according to a meta-analysis done in 2005.

A Cochrane systematic review in 2017 concluded that video laryngoscopy, irrespective of blade design (Macintosh style, hyper-angulated style, Miller style, or straight style) provides better glottic views and increases rate of successful first attempt intubation, with the hyper angulated designs improving the rate of successful intubation in individuals with features of difficult airway. Successful first-attempt intubation was superior in the video laryngoscope group (85%) compared to the direct laryngoscope group (70.8%) in critically ill patients.

While intubations are frequent procedures and generally safe, additional complications of difficult intubation include vocal cord paralysis, laryngeal nerve injury including laryngeal nerve palsy, oral and dental injuries, mucosal lacerations, laryngotracheal stenosis, edema, granulomas, vocal fold hematomas, ulcerations, arytenoid dislocation, vocal fold motion impairment, and other temporary or long-term related traumas. Thus, there remains a need for an improved laryngoscope device and method for improving proper placement of endotracheal tubes regardless of operator skill level.

A 2021 study by Biordsky, et. al. found that the most prevalent patient complaints following intubation were dysphagia (43%), pain (38%), coughing (32%), a sore throat (27%), and hoarseness (27%). The authors further found injuries reported in 20% of patients following intubation with edema the most frequently reported mild injury (9%-85% prevalence) and vocal fold hematomas the most frequently reported moderate injury (4% prevalence). Considering 1-in-5 patients in the studies reported injuries following intubation, such a widespread problem highlights the issues with conventional intubation methods and devices.

While most intubation-induced injuries are mild, such injuries can hinder quality of life. A 2018 study by Sung et. al. found that intubation can affect voice outcomes adversely for 1 week post-operatively. A 2000 study to Friedrich et. al. found direct lesions including oedema, rubor, haematoma, granuloma in approximately 4.7% of patients following intubation and permanent intubation-related recurrent nerve palsy in 0.5% of patients.

One complication in particular, vocal cord paralysis (VCP), is especially serious as it predisposes aspiration and the possible death of patients. In a 2019 study, Lim et. al. found that VCP persisted until a final follow-up examination in over 30% of the patients they examined with laryngoscopy-induced VCP.

A 2020 article by Evman, et. al. found that unilateral vocal cord paralysis due to intubation is more common than bilateral paralysis. In a 2019 study examining closed claims of vocal cord injuries related to endotracheal intubation by Homsi et. al., the authors found that 65% of the claims were deemed "permanent minor." In their study, Homsi et. al. found "technical knowledge/performance" to be the most common contributing factor and "trauma from endotracheal tube placement" the most common plaintiff allegation. The top alleged complications included bilateral vocal cord paralysis, unilateral (left-sided) vocal cord paralysis, and laryngeal nerve injury. Such findings highlight the need for an improved intubation device and method that is easier to use.

Intubation is more difficult in emergency settings in which every second matters. A 2014 study by Pacheco-Lopez et. al. found that the incidence of difficult intubation is 8-12% in emergent settings compared to 6% of elective procedures, respectively. Pacheco-Lopez et. al. found that complications increase 7-fold after second and third laryngoscopy attempts. Additionally, Pacheco-Lopez et. al. highlight an issue in which blind insertion of the endotracheal tube may further contribute to oropharyngeal injuries. Thus, there not only is a need for an improved fast, efficient laryngoscopy method, but one that also provides continuous visualization of the endotracheal tube throughout intubation as well.

One of the video laryngoscopes available in the market, the GlideScope®, has a blade similar to the Macintosh blade but with a pronounced 60° angulation. On the inferior aspect of the blade is a video camera that provides a wide visual field at the level of the glottis. According to Aziz et. al., the success rate of endotracheal intubation using the GlideScope® as a primary technique was 98%, compared to 96% in patients predicted to be difficult on direct laryngoscopy. After failed direct laryngoscopy, the success rate was 94% with the GlideScope®. A failure rate of 6% of the millions of annual intubations worldwide is a problematic number and therefore an improvement of the technique of intubation is needed. Similarly, video laryngoscopy has been shown to be comparable or superior to direct laryngoscopy when it comes to glottic view. It has also been found to facilitate intubation when direct laryngoscopy was predicted to be difficult. A malleable stylet is always recommended to be used with a video laryngoscope to facilitate directing the ETT to the glottis. Nevertheless, intubation might fail when using a video laryngoscope, since during the intubation process, intubating stylets cannot be actively adjusted. Thus, even when the glottis is properly visualized, the operator might not be able to direct the tube toward the vocal cords.

Flexible fiber-optic laryngoscopy has been established to be a successful method for endotracheal intubation in cases of anticipated difficult airway as well as a rescue technique, where the success rate was found to be 85.2% at the first attempt, reaching 93.9% within 3 min, in a study that evaluated 1612 cases by Heidegger et al. However, in one study that assessed nasotracheal fiber-optic intubation, 3 out of 413 cases were unsuccessful due to difficulty in advancing the ETT over the fiberscope. Reasons behind failure included the inability to visualize the larynx, direct a tube toward the larynx, or advance the tube over the fiber-optic bronchoscope. Another study showed that the right aryte-noid cartilage was the most frequently impinged structure during the passage of the ETT into the trachea.

In 2020, GlideScope® Core came afterward. It combines the GlideScope® video laryngoscope with a BFlex single-use bronchoscope on one screen showing both views simul-taneously. However, this advanced multimodal airway man-agement requires two operators. The role of the first operator is to insert the GlideScope® to visualize an optimal glottic view, then the second operator holds the GlideScope® in a fixed position to maintain the same view, while the first operator inserts the fiberscope and advances the ETT into the trachea. One study compared GlideScope® Core, C-mac Miller and conventional Miller laryngoscope for difficult airway management in simulated Pierre Robin sequence (PRS). Failure rate was 14% with GlideScope® Core, despite having the best glottic view, attributed to the inherent anatomical complexity of PRS. The aim of the present disclosure is to improve the failure rate of 14% due to the difficulty directing the fiber-optic scope whereby the scope gets lost in the oropharynx of the patient and therefore it would be difficult to direct the fiber-optic scope to the vocal cords. Using our method, the scope will be guided in the channel towards the vocal cords. This enables a faster insertion of a guidewire, such as a bougie or fiber-optic scope, into the vocal cords without wasting precious seconds in a patient that is anesthetized, paralyzed, and not breathing. The faster to reach intubation in an anesthetized patient, the less risk of desaturation or hypoxia or more serious com-plications not limited to cardiac arrest if the mask ventilation was not successful.

SUMMARY

The present disclosure relates to laryngoscope blade modification for endotracheal intubation. The present dis-closure relates to laryngoscope blade with a channel that could be flexible with a slit or rigid, opening via a spring system to facilitate the endotracheal intubation. The disclo-sure provides a channel which is attached to the laryngo-scope blade of either a direct laryngoscope or video laryn-goscope. The channel further incudes a slit along the entire portion of the channel. The endotracheal tube (ETT) may be loaded on a guidewire, such as a flexible bougie, fiber-optic scope, or a spring wire, that has a soft tip that can be directed up and down and right and left in the same way that a fiber-optic scope operates. The guidewire is inserted into the laryngoscope blade via the channel and the tip of the guidewire shall not go beyond the camera level of the video laryngoscope. The endotracheal tube (ETT) is preloaded on the guidewire. When used with a direct laryngoscope, a preferred guidewire option would be a fiber-optic scope however a bougie may be used as well.

In some example embodiments, an apparatus comprises a blade, a channel attached to the blade, wherein the channel includes a slit along an entire portion of the channel, and a guidewire that includes a soft tip that can be directed up and down, wherein the guidewire is inserted into the blade via the flexible channel, wherein the guidewire is dislodged out of the channel through the slit present on the channel. In one embodiment, opposing edges of the slit are configured to contact each other, maintaining a closed position during intubation and preventing ingress of liquid into the channel while being configured to allow the guidewire to be removed from the channel when the endotracheal tube is being inserted.

The present disclosure enables faster intubation than conventional methods as the channel enables a guidewire to be quickly dislodged and endotracheal tube inserted in a quick, efficient manner. Given that improper placement of endotracheal tubes is a significant contributor to intubation-related complications, the easy-to-use, precise device helps mitigate many of the complications resulting from conven-tional methods. The present disclosure also helps enable a clear line of vision for operators of both direct and video laryngoscopes and laryngoscope blades.

The device and method of the present disclosure is beneficial for patients of all ages requiring intubation. This is especially true for pediatric patients where conventional methods using a rigid stylet inserted into endotracheal tubes are often traumatic to pediatric patient's vocal cords and fail to meet the vocal cords during intubation attempts. Addi-tionally, in difficult pediatric airways when a fiber-optic scope is used, the use of a pediatric fiber-optic scope greatly impairs the vision of the vocal cords. Such vision difficulty is due to the fiber-optic scope curling in the oropharynx of the pediatric patient. In the present disclosure, the fiber-optic scope is held by the laryngoscope blade and advanced easily towards the cords without curling by allowing the tip of the fiber-optic scope to directly meet the vocal cords. Such an improvement over conventional devices and methods reduces the time to intubation which is crucial in emergency situations. Additionally, the use of a bougie or a fiber-optic scope with a soft tip in the present disclosure avoids the trauma to the vocal cords.

Another benefit of the present disclosure is that the channel provides a streamlined route to a patient's vocal cords. This avoids curling seen in conventional devices and methods as well as secretions and soft tissue that are significant barriers to successful intubation. As opposed to GlideScope® Core which combines a video laryngoscope with a single use BFlex bronchoscope, which is very expen-sive for institutions, the present disclosure only requires a laryngoscope and guidewire to operate effectively.

Additional aspects, advantages, features, and objects of the present disclosure will be made apparent from the drawings and the detailed description of the illustrative embodiments construed in conjunction with the appended claims that follow.

It will be appreciated that features of the present disclo-sure can be combined in various combinations without departing from the scope of the present disclosure as defined by the appended claims.

BRIEF DESCRIPTION OF THE DRAWINGS

The summary above and the following detailed descrip-tion of illustrative embodiments are better understood when read in conjunction with the appended drawings. To illus-trate the present disclosure, exemplary constructions of the disclosure are shown in the drawings. However, the present disclosure is not limited to specific methods and instrumen-talities disclosed herein. Moreover, the drawings are not to scale. Wherever possible, like elements have been indicated by identical numbers.

Embodiments of the present disclosure are described, by way of example only, with reference to the following diagrams wherein.

It will be appreciated that the drawings illustrated herein are for representation purposes only and do not intend to limit the scope of the present disclosure. Actual implementation of the present disclosure may be different.

DETAILED DESCRIPTION

The following description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The drawings disclose illustrative embodiments and represent graphical summaries of the data explained and described herein. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it is intended to refer to the same or like components or steps.

Figure 1:
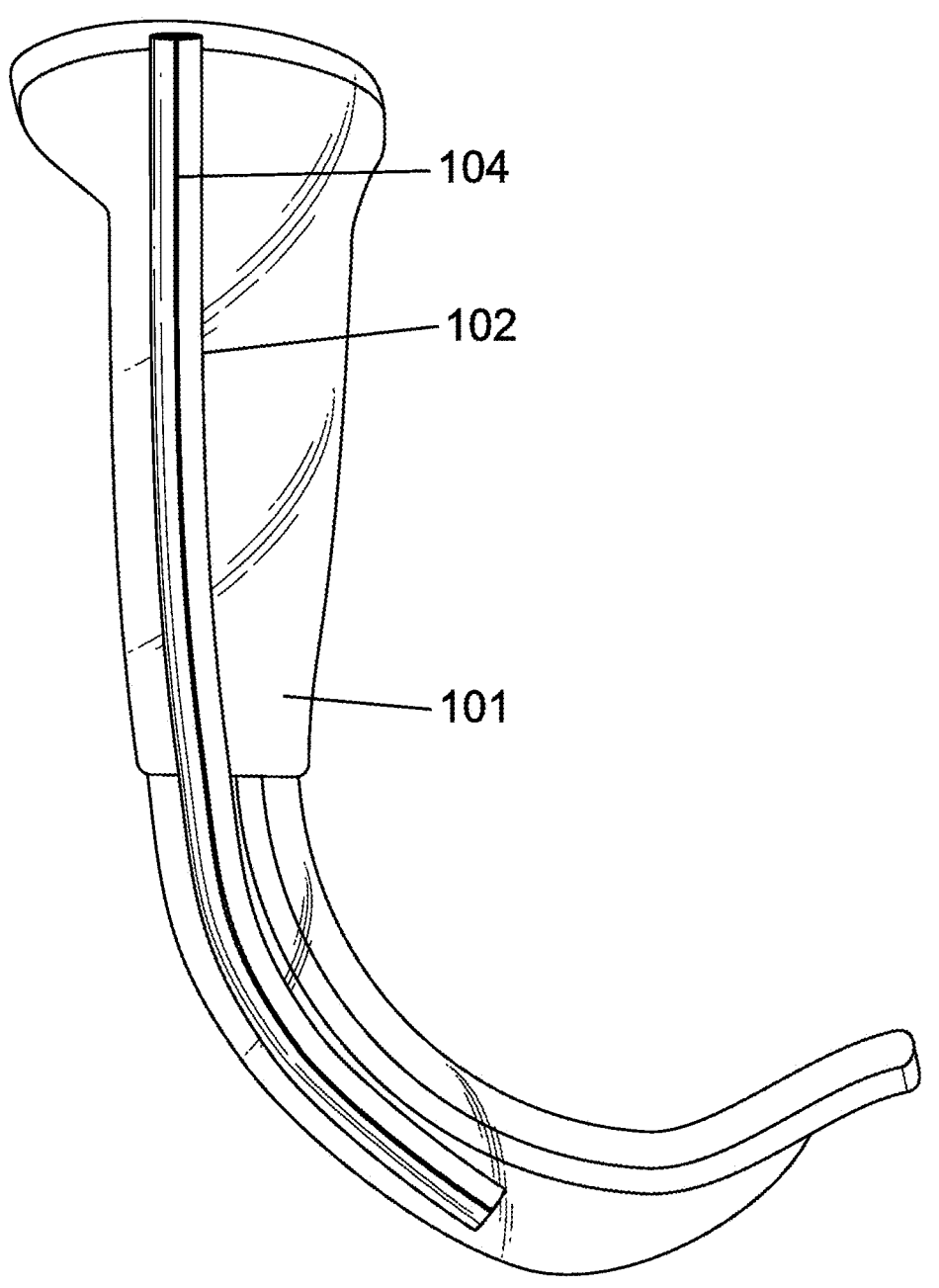
FIG. 1 depicts a channel 102 attached alongside of a video laryngoscope blade or direct laryngoscope blade, according to the one embodiment of the invention.

FIG. 1 depicts a channel 102 attached alongside of a laryngoscope blade 101, according to one embodiment of the invention. Laryngoscope blade 101 includes laryngoscope blades 101 for use with video laryngoscopes or direct laryngoscopes. Referring to FIG. 1, the present invention describes a channel 102 which is attached to the laryngoscope blade 101. One possible way to attach the channel 102 onto the laryngoscope blade 101 is by using a plurality of straps or buckles to secure the channel 102 to the laryngoscope blade 101. However, the attachment shown herein is illustration purpose any other possible ways of attachment may be also implemented without varying the scope and usage of a channel 102. In a preferred embodiment, channel 102 is flexible. In an alternative embodiment where channel 102 is rigid, channel 102 may be molded to the laryngoscope blade 101. Laryngoscope refers to both video laryngoscope or direct laryngoscope.

In some example embodiments, the laryngoscope blade 101 is shown herein is for illustrative purpose. However, the laryngoscope blade 101 may be of any type, including laryngoscope blades 101 of video laryngoscopes or direct laryngoscopes. The laryngoscope blade 101 may be curved, for example Macintosh-type blades, or straight, for example Miller-type blades. The shape of the channel 102 is adapted to adjust according to the size and shape of the laryngoscope blade 101.

Figure 2:
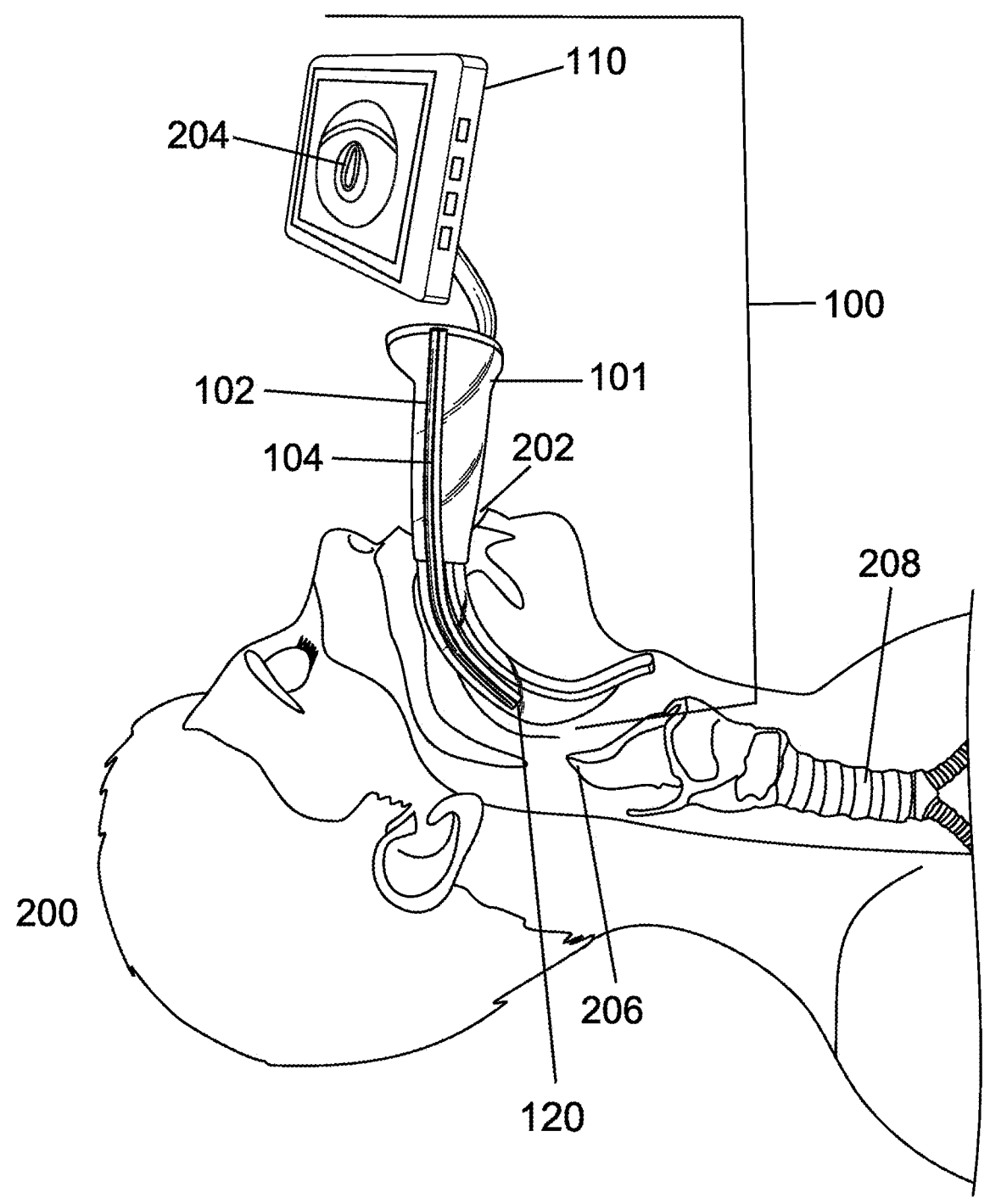
FIGS. 2-10 depict the endotracheal intubation using a video laryngoscope blade which is described in FIG. 1.

FIG. 2 depicts the visualization of the vocal cords using the laryngoscope blade 101 illustrated in FIG. 1. In some example embodiments, the laryngoscope 100 is exemplified herein for illustrative purposes. In some example embodiments, a direct laryngoscope is inserted instead of a video laryngoscope. However, the channel 102 and the guidewire 106 remain the same regardless of a direct laryngoscope or video laryngoscope being used for endotracheal intubation as well as laryngoscope blade 101 shape.

FIG. 2 depicts a laryngoscope 100 inserted in the mouth 202 of the patient 200. In this embodiment, the laryngoscope 100 is a video laryngoscope. Once the patient 200 is put to sleep, the laryngoscope 100 is inserted in the mouth 202 of the patient 200 and advanced until the vocal cords 204 are seen on the screen 110 of the video laryngoscope.

In some example embodiments, at the time of insertion of the video laryngoscope, an assistant (human) may hold the laryngoscope 100 in place securing the vision of the vocal cords 204 at all times.

Figure 3:
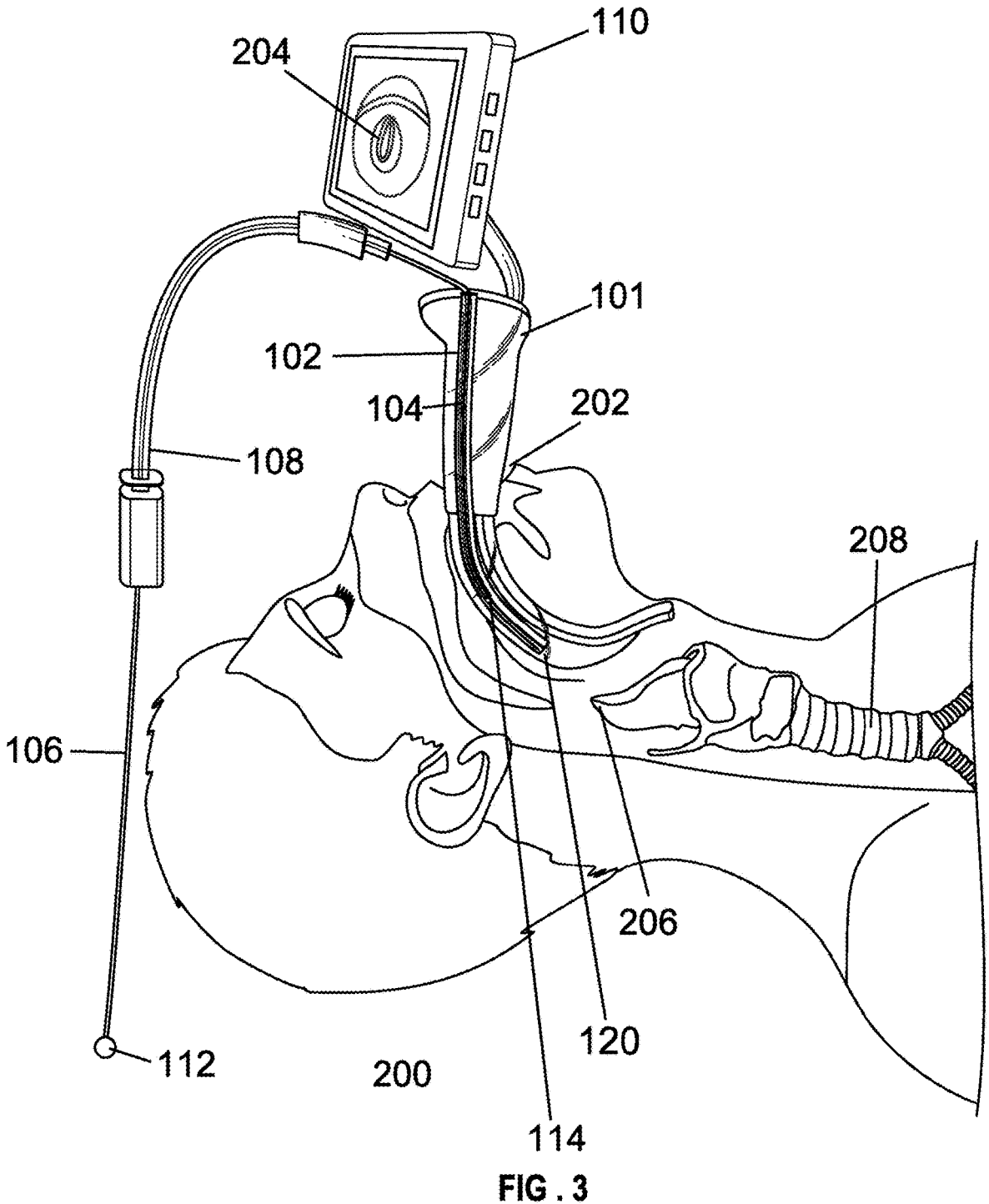

Referring to FIG. 3, the guidewire 106 is inserted into the laryngoscope blade 101 via the channel 102 such that the tip 114 of the guidewire 106 shall not go beyond the camera level 120 of the laryngoscope 100. In some example embodiments, the endotracheal tube 108, hereinafter "ETT tube", may be loaded on a guidewire 106 that is flexible and has a tip 114 that is both soft and can be directed up and down in the same way that a fiber-optic scope operates. In some example embodiments, in the absence of such a guidewire 106, a fiber-optic scope may be used as an alternative. In some example embodiments, the guidewire 106 is preloaded in the channel 102 of the laryngoscope blade 101 before the patient 200 is put to sleep. In one embodiment where a direct laryngoscope is used without assistance of a screen 110, the operator may use their vision through the laryngoscope 100 to direct the guidewire 106 into the vocal cords 204 of the patient 200. In one example, operator may refer to medical doctor.

Figure 4:
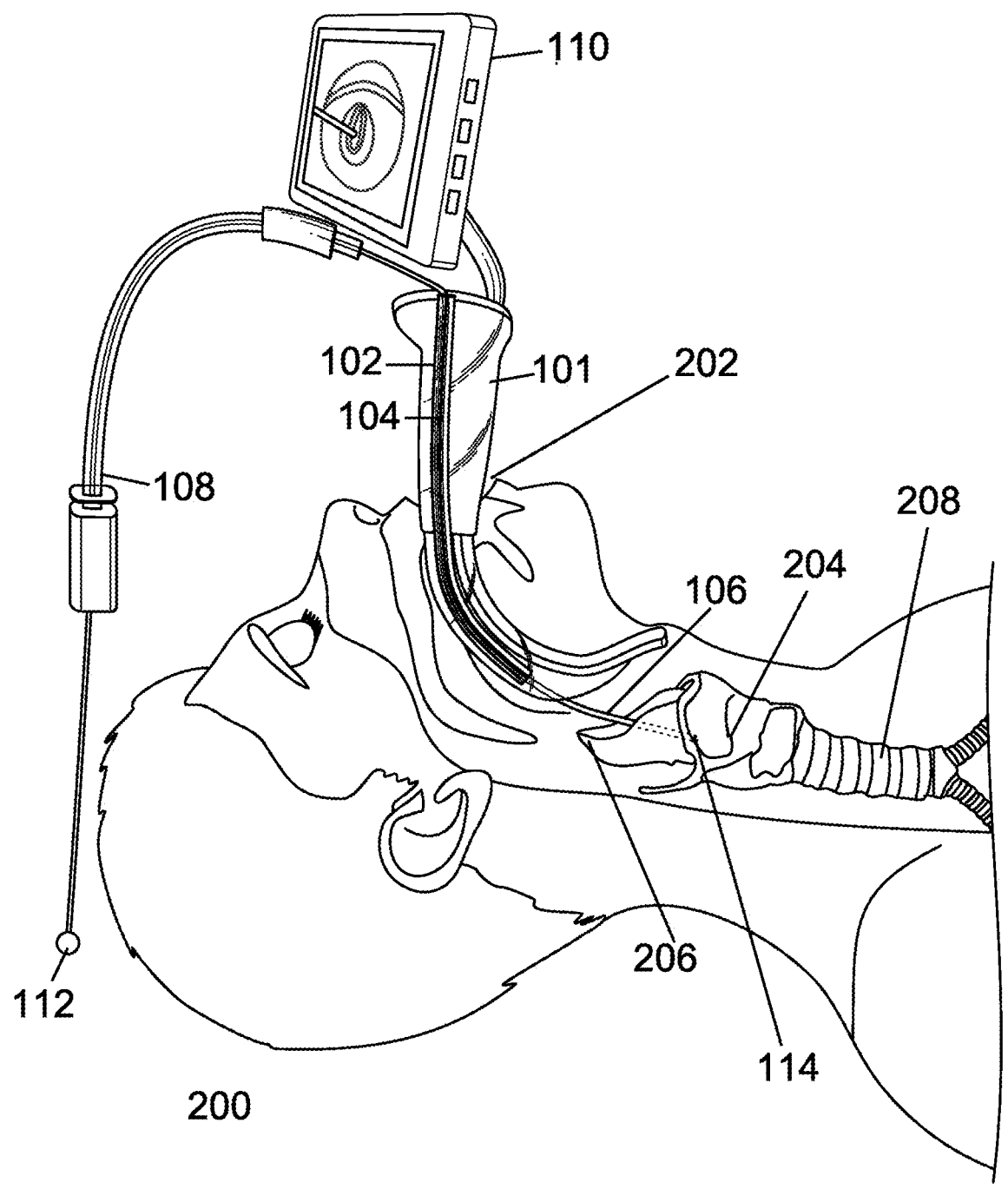

FIG. 4 depicts the guidewire 106 being advanced towards the epiglottis 206 of the patient 200 and through the vocal cords 204. In some example embodiments, a second operator will hold the laryngoscope 100 still once the vocal cords 204 are identified, subsequently the first operator, such as a anesthesiologist, will free his/her both hands and will be able to advance the guidewire 106 with one hand and with the opposite hand will flex up and down or left and right the tip 114 of the guidewire 106 aiming towards the vocal cords 204. A control 112 on a proximal end of the guidewire 106, such as a dial, switch, button, or the like, is used by an operator to move the tip 114 up and down or left and right. In some example embodiments, once the guidewire 106 enters the vocal cords 204 it will be advanced for many cm (5-6 cm in adults and 3-4 cm in pediatric patients).

Figure 5:
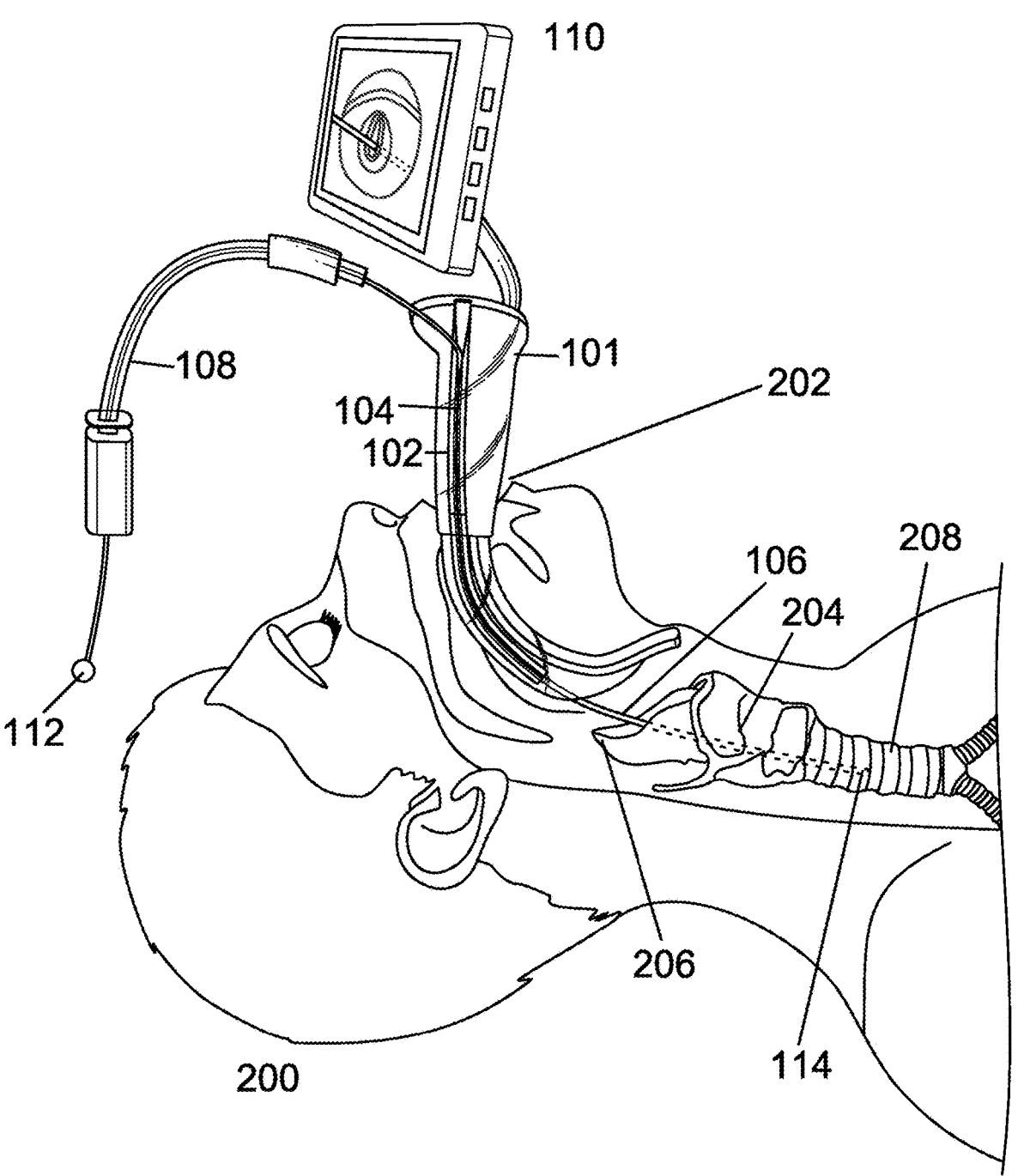

FIG. 5 depicts the guidewire 106 being dislodged from the slit 104 of the channel 102. In some example embodiments, the anesthesiologist will dislodge the guidewire 106 out of the channel 102 through the slit 104 present on the channel 102. This dislodgement will be done as much as possible (as much as the anesthesiologist can reach in the mouth 202, usually few cm).

Figure 6:
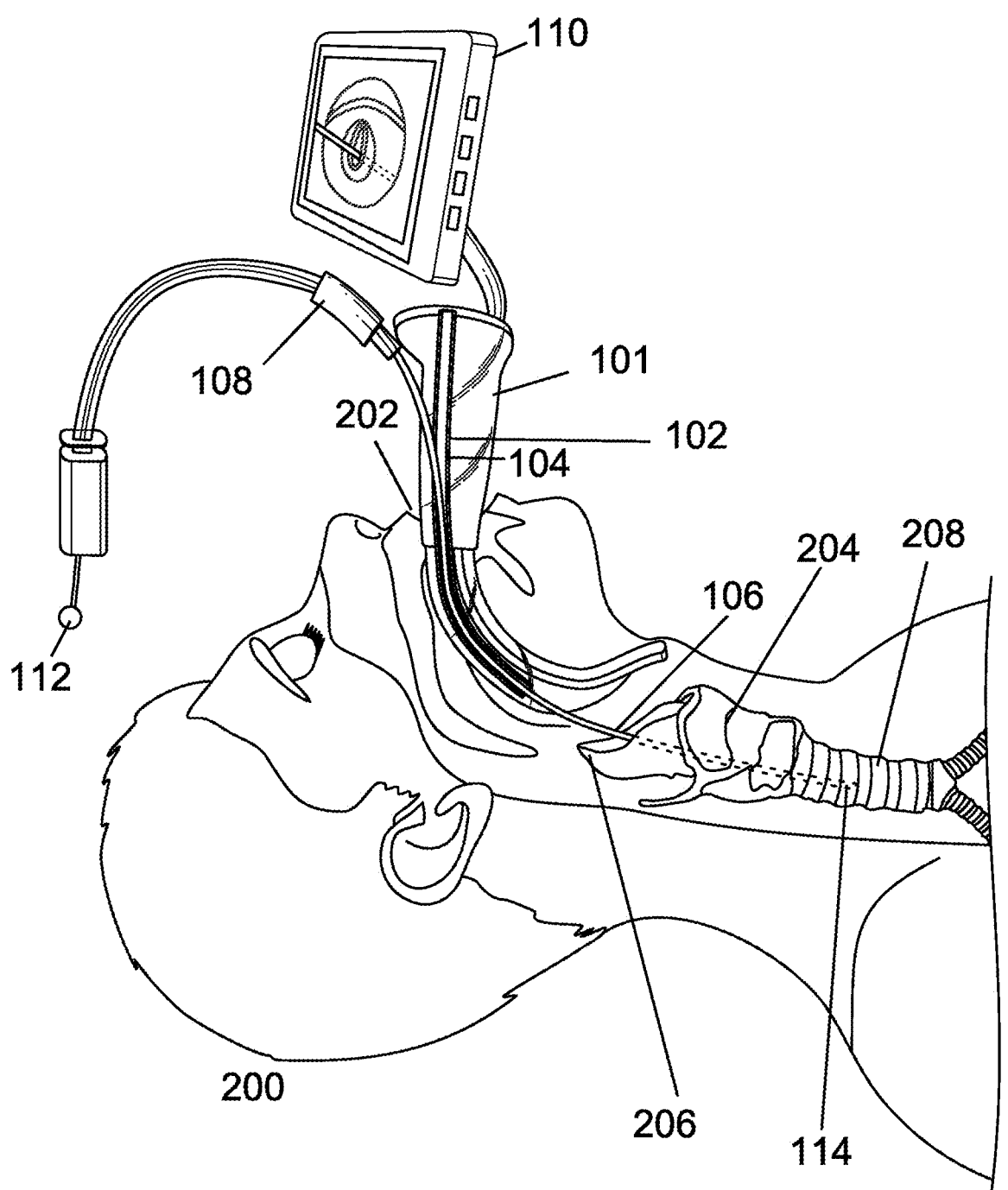

FIG. 6 depicts the time at which the ETT tube 108 is advanced into the patient 200 oropharynx. In some example embodiments, the advancement of the ETT tube 108 will ensure the complete dislodgment of the guidewire 106 out of the channel 102 through the slit 104. In this embodiment, channel 102 is soft.

Figure 7:
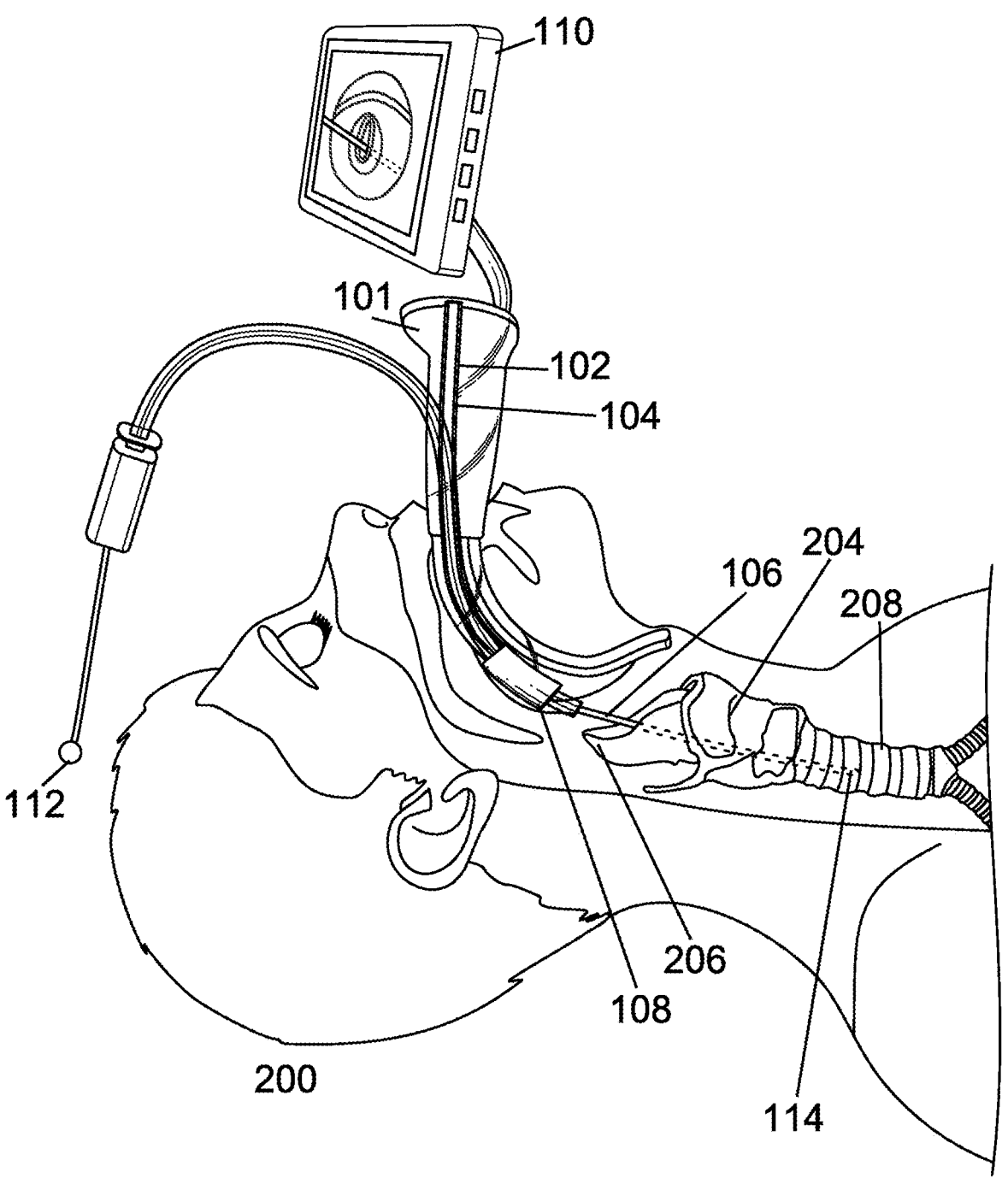
Figure 8:
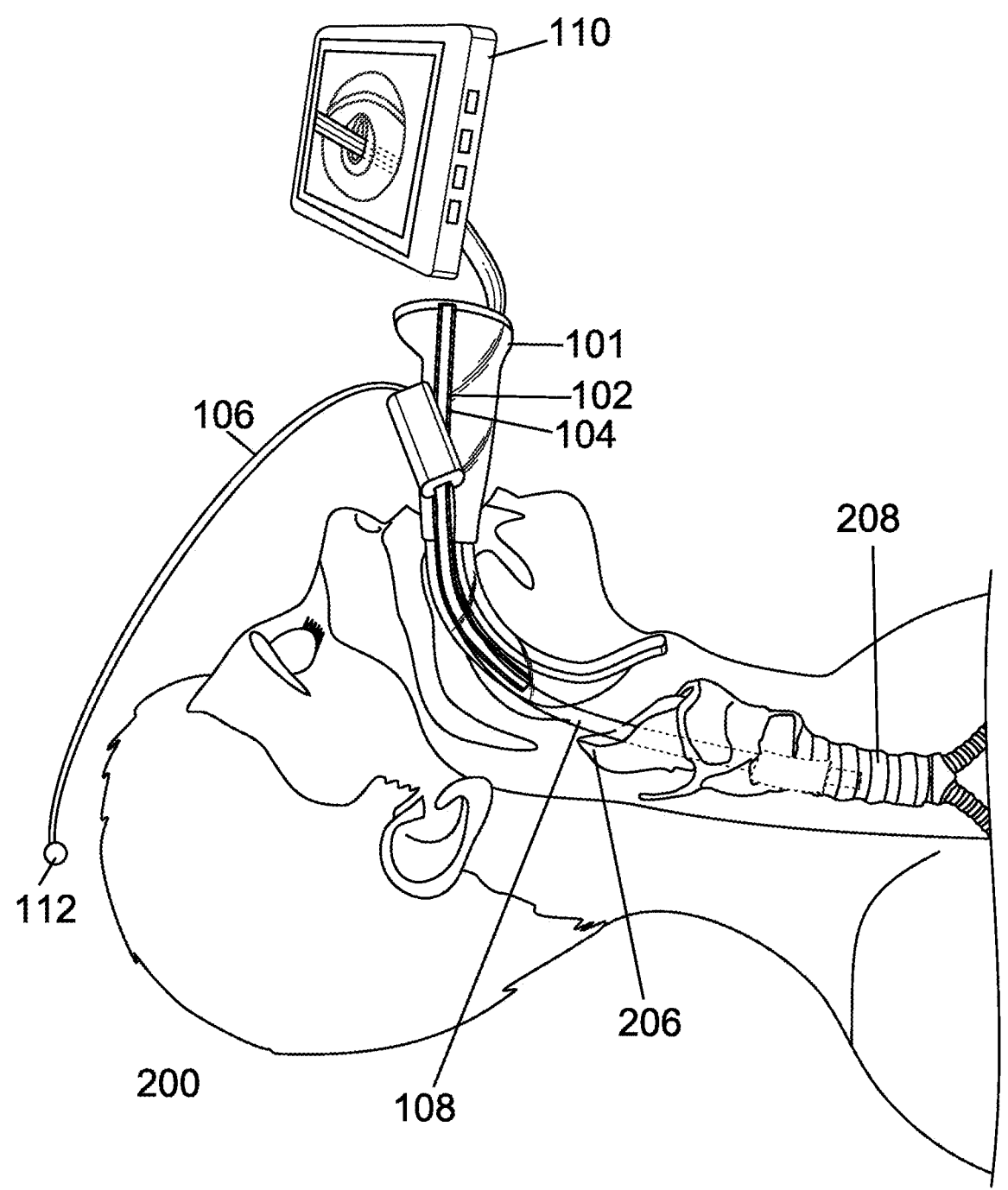

As depicted in FIG. 7 and FIG. 8, in some example embodiments, the ETT tube 108 will be advanced all the way down into the vocal cords 204 and the trachea 208. The successful intubation will be seen and confirmed on the screen 110 of a video laryngoscope. In one embodiment where a direct laryngoscope is used without video capabilities, the placement of the ETT tube 108 will be visually confirmed by the operator through the laryngoscope using direct vision. The method of the current disclosure can be used during direct laryngoscopy without the use of video laryngoscope. The channel 102 is attached to the laryngoscope blade, using any type of blade, including curved blades (i.e. macintosh blades) or straight blades (i.e. Miller blades). Such blades may be used with video laryngoscopes or direct laryngoscopes.

In some example embodiments, after the successful intubation and correct positioning of the ETT tube 108 level will be ensured. Advancement of the ETT tube 108 will stop once the cuff of the ETT tube 108 is beyond the vocal cords 204 in case of a cuffed ETT tube 108 is used which is the case for adult patients, adolescents, and pediatric patients. In some pediatric cases, uncuffed ETT tube 108 are used and the advancement of the ETT tube 108 will stop at the mark seen on the ETT tube 108.

Figure 9:
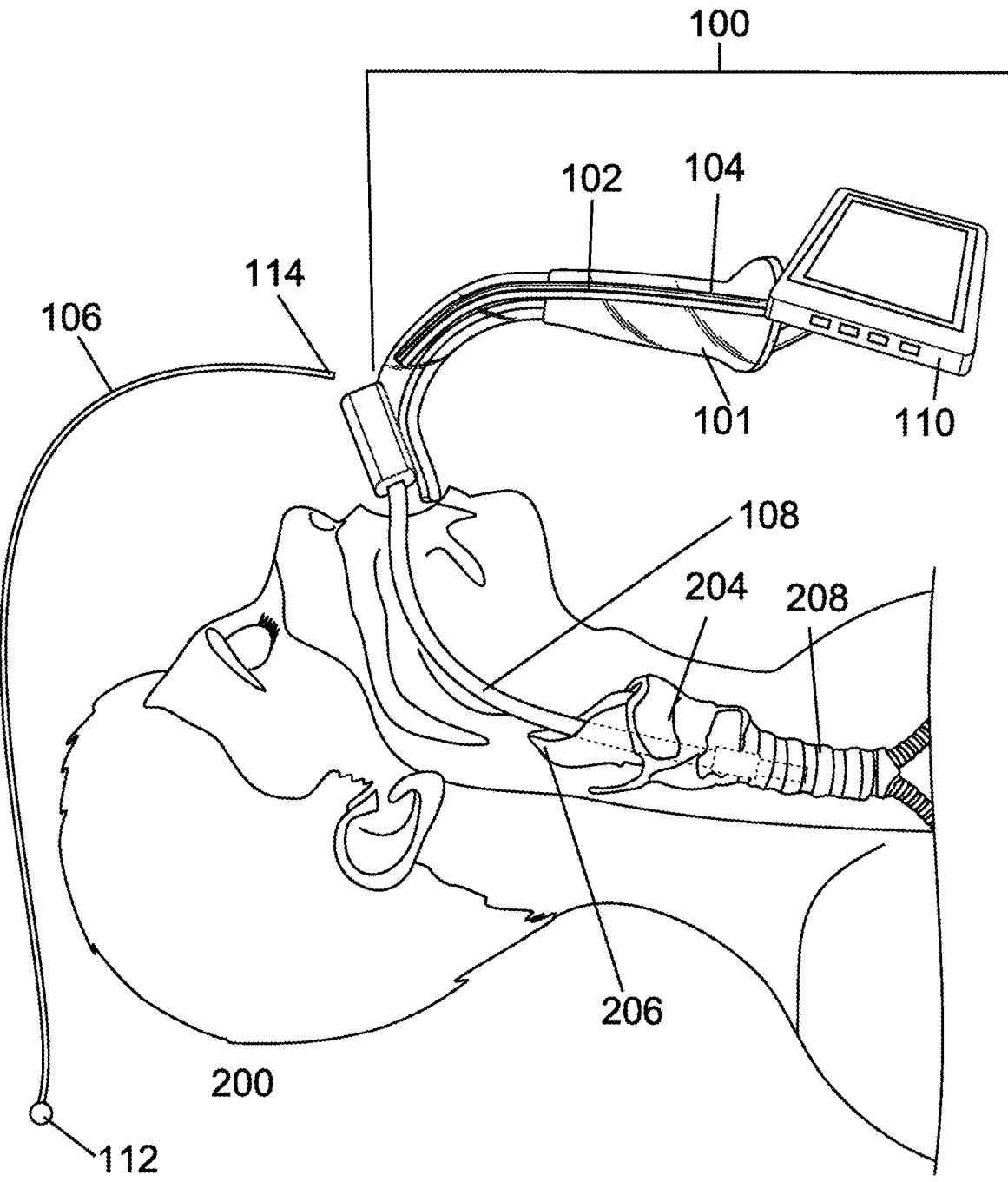

FIG. 9 depicts the guidewire 106 being removed from the ETT tube 108. In some example embodiments, the next step will be removal of the guidewire 106 from the ETT tube 108, and connecting the ETT tube 108 to an anesthesia machine circuit. The removal of the laryngoscope blade 101 and taping of the ETT tube 108 to secure it in place will follow.

Figure 10:
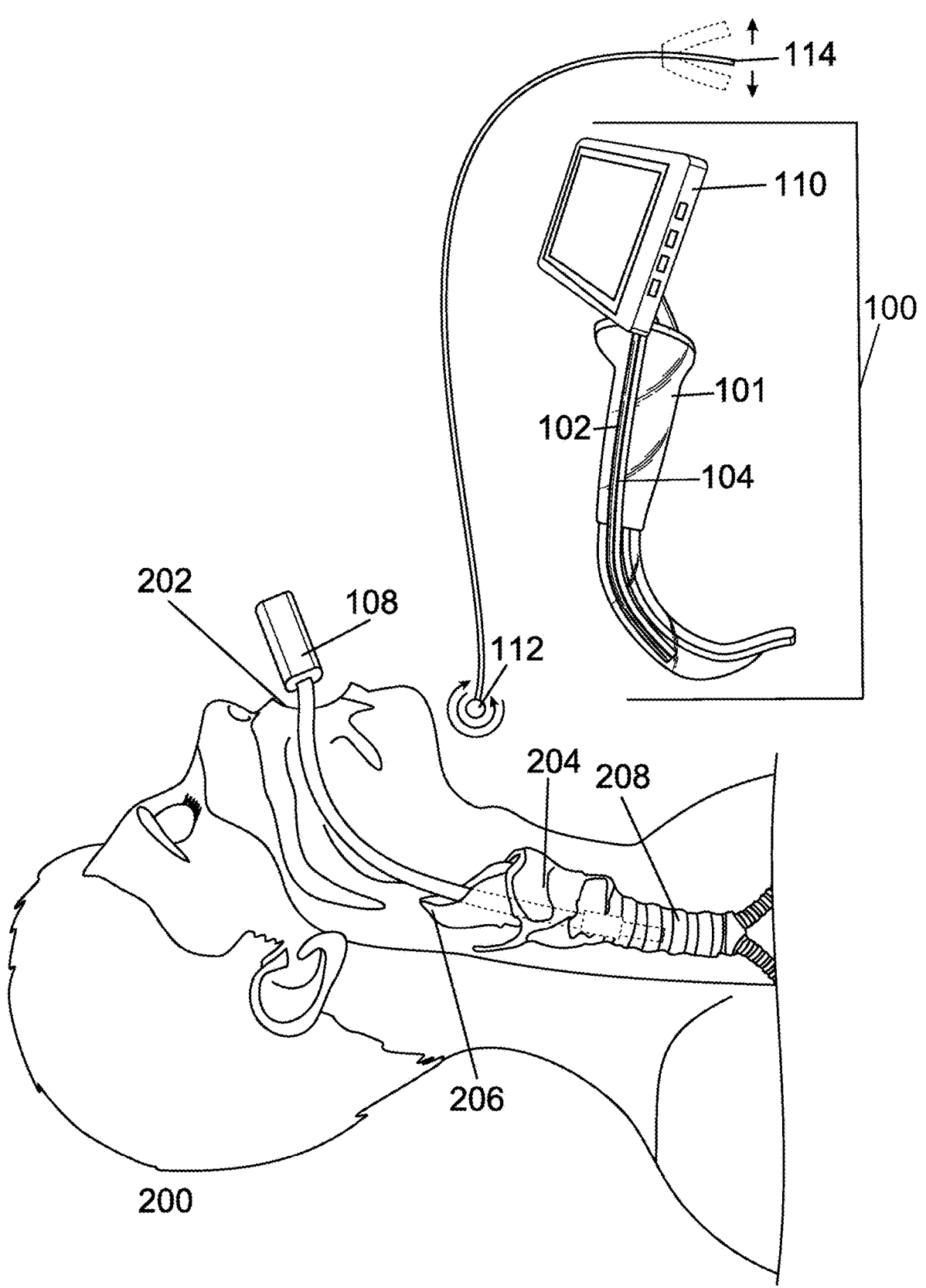

FIG. 10 depicts the control 112 of the proximal end of the guidewire 106 controlling the tip 114 on the distal end of the guidewire 106. In this embodiment, control 112 is a dial which may be rotated clockwise or counterclockwise to facilitate up and down movement of the tip 114. In other embodiments, tip 114 may be moved up and down or left and right by a dial, switch, button, or like.

Although presented as numbered steps, the steps of these methods herein can be performed at a same time or in a different order. Additionally, portions of these steps may be used with portions of other steps from other methods. Also, all or portions of a step may be optional. Additionally, any of the steps of any of the methods can be performed out of order or in a different order and can be performed with modules, circuits, or other known means for performing these steps.

The specific details of particular embodiments may be combined in any suitable manner without departing from the spirit and scope of embodiments of the invention. However, other embodiments of the invention may involve specific embodiments relating to each individual aspect, or specific combinations of these individual aspects. The above description of exemplary embodiments of the invention has been presented for the purpose of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "of" is intended to mean an "inclusive or," and not an "exclusive or" unless specifically indicated to the contrary.

What is claimed is:

1. An apparatus for facilitating the insertion of an endotracheal tube during endotracheal intubation, comprising:
   a laryngoscope blade having a length and a width; and
   a guidewire channel having a length and a width sized to slidably receive a guidewire with a slit having opposing edges along the length of the guidewire channel, wherein the opposing edges of the slit contact each other to create a closed position, attached to the laryngoscope blade wherein the guidewire channel directs the guidewire the length of the laryngoscope blade and the slit prevents ingress of liquid into the guidewire channel and allows the guidewire to be removed from the guidwire channel when the endotracheal tube is advanced onto the guidewire outside of the guidewire channel and wherein the slit returns to the closed position and the prevention of ingress of liquid is maintained after the guidewire has been removed; wherein the guidewire channel has an inner cross-sectional dimension sufficient to permit passage of the guidewire and insufficient to permit passage of an endotracheal tube.

2. The apparatus of claim 1, wherein the guidewire channel is attached alongside of the laryngoscope blade.

3. The apparatus of claim 1, wherein the guidewire may be a fiber-optic scope.

4. The apparatus of claim 1, wherein the laryngoscope blade is a straight blade.

5. The apparatus of claim 1, wherein the laryngoscope blade is a curved blade.

6. The apparatus of claim 1, wherein the laryngoscope blade is attached to a video laryngoscope.

7. The apparatus of claim 1, wherein the laryngoscope blade is attached to a direct laryngoscope.

8. The apparatus of claim 1, whereby the guidewire channel is a flexible guidewire channel molded to the laryngoscope blade.

9. The apparatus of claim 1, wherein the guidewire channel is molded to the laryngoscope blade.

10. The apparatus of claim 1, wherein the guidewire channel is secured to the laryngoscope blade using tape.

11. A method of endotracheal intubation, the method comprising:
   securing a guidewire channel to a video laryngoscope blade;
   loading an endotracheal tube on a guidewire;
   loading the guidewire into the guidewire channel of the video laryngoscope blade;
   inserting the video laryngoscope into the mouth of the patient;
   advancing the video laryngoscope into the oropharynx of the patient;
   finding the vocal cords of the patient on a video laryngoscope screen;
   advancing the guidewire towards the vocal cords of the patient;
   advancing guidewire into the trachea of the patient;
   dislodging the guidewire partially from the guidewire channel of the video laryngoscope through a slit in the guidewire channel while maintaining the slit in a closed position relative to the guidewire to prevent liquid ingress into the guidewire channel;
   advancing the endotracheal tube over the guidewire to completely dislodge the guidewire from the guidewire channel wherein the slit returns to a closed position after dislodgment;
   advancing the endotracheal tube outside of the guidewire channel into the oropharynx of the patient;
   advancing the endotracheal tube towards the vocal cords of the patient;
   advancing endotracheal tube into the trachea of the patient;
   confirming, the placement of the endotracheal tube, by visualizing the endotracheal tube going through the vocal cords of the patient;
   stopping the advancement of the endotracheal tube, once a cuff of the endotracheal tube is beyond the vocal cords of the patient;

removing the guidewire from the endotracheal tube;

removing the laryngoscope from the mouth of the patient; and fastening, the endotracheal tube in place to the patient; wherein the guidewire channel has an inner cross-sectional dimension sufficient to permit passage of the guidewire and insufficient to permit passage of an endotracheal tube.

12. A method of endotracheal intubation, the method comprising:

attaching a guidewire channel to a direct laryngoscope blade;

loading an endotracheal tube on a guidewire;

loading the guidewire into the guidewire channel of the direct laryngoscope;

inserting the direct laryngoscope in the mouth of the patient;

advancing the direct laryngoscope into the oropharynx of the patient;

finding, using direct inspection by an operator, the vocal cords of the patient;

advancing the guidewire towards the vocal cords of the patient;

advancing the guidewire into the trachea of the patient;

dislodging the guidewire partially from the guidewire channel of the direct laryngoscope through a slit in the guidewire channel;

dislodging the guidewire partially from the guidewire channel of the direct laryngoscope through a slit in the guidewire channel while maintaining the slit in a closed position relative to the guidewire or fiber-optic scope to prevent liquid ingress into the guidewire channel;

advancing the endotracheal tube over the guidewire to completely dislodge the guidewire from the guidewire channel wherein the slit returns to a closed position after dislodgment;

advancing the endotracheal tube outside of the guidewire channel into the oropharynx of the patient;

advancing the endotracheal tube into the vocal cords of the patient;

advancing the endotracheal tube into the trachea of the patient;

confirming, the placement of the endotracheal tube, using direct inspection by the operator;

stopping the advancement of the endotracheal tube, once an endotracheal tube cuff is beyond the vocal cords of the patient;

removing the guidewire from the endotracheal tube;

connecting the endotracheal tube to an anesthesia machine circuit;

removing the laryngoscope from the mouth of the patient; and securing the endotracheal tube in place to the patient; wherein the guidewire channel has an inner cross-sectional dimension sufficient to permit passage of the guidewire and insufficient to permit passage of an endotracheal tube.

13. The method of claim 12, wherein the guidewire is a bougie or a fiber-optic scope.

* * * * *